US007854936B2

(12) United States Patent
Bishop et al.

(10) Patent No.: US 7,854,936 B2
(45) Date of Patent: Dec. 21, 2010

(54) ANTI-INFLAMMATORY HYDROLYSATE OF C. VERSICOLOR

(75) Inventors: Michael Bishop, Dallas, TX (US);
Elysiann Bishop, Dallas, TX (US);
Walter Smith, Wellington, FL (US);
Glen Gillis, Denton, TX (US)

(73) Assignee: Active Organics, Inc., Lewisville, TX (US)

( * ) Notice: Subject to any disclaimer, the term of this patent is extended or adjusted under 35 U.S.C. 154(b) by 367 days.

(21) Appl. No.: 12/007,654

(22) Filed: Jan. 14, 2008

(65) Prior Publication Data

US 2009/0181047 A1 Jul. 16, 2009

(51) Int. Cl.
*A61K 36/06* (2006.01)
*A61K 36/09* (2006.01)

(52) U.S. Cl. .................................. 424/195.15
(58) Field of Classification Search .............. None
See application file for complete search history.

(56) References Cited

U.S. PATENT DOCUMENTS

2005/0175640 A1* 8/2005 Yamada et al. .............. 424/400

FOREIGN PATENT DOCUMENTS

EP 0504947 A2 * 9/1992

OTHER PUBLICATIONS

Cui et al., Polysaccharopeptides of *Coriolus versicolor*: physiological activity, uses, and production, 2003, Biotechnology Advances, 21: 109-122.*
Sumantha et al.. Microbiology and Industrial Biotechnology of Food-Grade Proteases: A Perspective, 2006, Food-Grade Proteases, Food Technol. Biotechnol, 44: 211-220.*

* cited by examiner

*Primary Examiner*—Christopher R. Tate
*Assistant Examiner*—Catheryne Chen
(74) *Attorney, Agent, or Firm*—Chalker Flores, LLP; Chainey P. Singleton; Edwin S. Flores

(57) ABSTRACT

Methods and compositions for reducing and/or inhibiting inflammation by topical application of dermatocosmetic compositions comprising effective amounts of extracts of *Coriolus versicolor* that have been hydrolyzed by an acid protease, preferably *Rhizomucor miehei,* and thereafter rendered substantially devoid of acid-protease activity.

9 Claims, No Drawings

ANTI-INFLAMMATORY HYDROLYSATE OF C. VERSICOLOR

FIELD OF INVENTION

The present invention relates to methods and compositions for reducing and/or inhibiting topical inflammation. More particularly, the present invention relates to topical application of dermatocosmetic products comprising effective amounts of extracts of Coriolus versicolor that have been hydrolyzed by an acid protease, preferably Rhizomucor miehei, and thereafter rendered substantially devoid of acid-protease activity.

BACKGROUND OF THE INVENTION

Prostaglandins are potent mediators of a wide range of physiological processes, including inflammation. Cyclooxygenase (COX) enzymes, also referred to as prostaglandin-endoperoxide synthases (PTGS), catalyze the rate limiting step in prostaglandin synthesis. Of the two cyclooxygenase enzymes, COX-2 enzyme (PTGS2) is inducible; it is produced in response to specific homeostatic changes. The discovery that COX-2 regulates the production of prostaglandins involved in the inflammation process, lead to the development of a class of agents that function as COX-2 inhibitors. Indeed, many anti-inflammatory agents now in the modern pharmacopoeia, including COX-2 inhibitors, have their origin in the practices of traditional medicine where plants and their extracts were administered to provide relief from pain, fever and inflammation. For example, the discovery that the active analgesic ingredients in Willow bark are salicylates, lead to the syntheses of acetylsalicylic acid (aspirin) and numerous other non-steroidal anti-inflammatory drugs (NSAIDs). Oral administration of these compounds is widely known to produce negative sequelae including irritation of the GI tract and bleeding. There has been, and remains a need, for efficacious topical anti-inflammatory compounds. With increased awareness of the potency of naturally-derived active agents, the need for such compounds is even more strongly felt.

The present invention is directed to a novel proteinaceous polysachharide extract of Coriolus versicolor, a mushroom with a history both in traditional Chinese botanical remedies as well as in modern biomedicine as an adjunct in cancer treatments. As described in further detail below, the compositions of the present invention are made by a heretofore unknown process in which proteinaceous polysaccharides extracted from the fruiting body of C. versicolor are solubilized in an aqueous solvent and then hydrolyzed with a specific acid protease enzyme derived from R. miehei, thus forming an extract with novel anti-inflammatory properties—specifically, the ability to reduce the expression of mRNA coding for PTGS2 by at least about 67% as measured by DNA microarray analysis using a full-thickness epidermal skin tissue model.

Two peptidic polysaccharides derived from Coriolus versicolor have been widely-studied for their antiproliferative and antitumor activities. The two protein-bound polysaccharides, designated as PSK and PSP, are isolated from the CM-101 and COV-1 strains of C. versicolor, respectively. PSP and PSK are chemically similar—both have molecular weights of approximately 100 kDa; both have glutamic acid and aspartic acid as the two most abundant amino acid residues; and both have monosaccharides with $\alpha$-1,4 and $\beta$-1,3 glucosidic linkages. The two compounds differ in that PSK contains fucose, while PSP contains rhamnose and arabinose. See, TB Ng. "A review of research on the protein-bound polysaccharide (polysaccharo-peptide, PSP) from the mushroom Coriolus versicolor (Basidiomycetes: Polyporaceae)" Gen Pharmacol Vol. 30, pp. 1-4 (1998).

PSK and PSP have also reported in the literature to have immuno-stimulatory effects. See TB Ng (1998) supra; see also Y. Dong, et al. "Antitumor effects of a refined polysaccharide peptide fraction isolated from Coriolus versicolor: in vitro and in vivo studies." Res. Commun. Mol. Pathol. Pharmacol. Vol. 92, pp. 140-148 (1996). PSK is commercially available under the tradename Krestin from Sankyo Co. Ltd. (Tokyo, Japan). See also, K K Chu, S S Ho and A H Chow, J. Clin. Pharmacol. Vol. 42, pp. 976-984 (2002)(describing traditional usage, pharmacological activities, clinical effects, adverse and reactions, active constituents of C. versicolor, J. Cui and Y. Chisti, Biotechnology Advances, Vol. 21, pp. 109-122 (review of the physiological activity, uses and methods for producing polysaccharopeptides from C. versiciolor).

While the prior art patent literature describes a number of processes for preparing polysachharide polypeptide fractions from C. versicolor, these references neither teach nor suggest the methods for producing the compounds of the present invention, nor the use of the product of this novel process (i.e., as a potent topical anti-inflammatory agent).

U.S. Pat. No. 4,051,314 is directed to oral administration of deproteinized polysaccharide hydrozylate derived from C. versicolor that produces anticarcinogenic activity in mice. Compositions claimed in the present invention are proteinaceous hydrolyzates.

U.S. Pat. No. 4,761,402 teaches use of PSK as a starting material for the preparation of a lyophilized soluble phosphorylated glucan that can be topically applied to treat infectious disease in animals or humans. The '402 Patent describes a soluble phosphorylated glucan prepared by a process comprising the steps of denaturing the three dimensional structure of a particulate glucan derived from C. versicolor followed by phosphorylation (mixing with phosphoric acid at a temperature of about 100° C. for several hours).

U.S. Pat. No. 4,818,752 describes the use of soluble phosphorylated glucan from C. versicolor prepared by the same process described in the '402 Patent and its use in treating malignant neoplastic disease in animals and humans.

U.S. Pat. No. 4,833,131 describes a soluble phosphorylated glucan from C. versicolor prepared by the same process described in the '402 Patent and its use in treating dermal wounds in animals and humans.

U.S. Pat. No. 5,374,714 describes a method of obtaining purified polypeptides from the COV-1 strain of C. versicolor by a specific process—High Performance Liquid Chromatography (HPLC) using an acid solvent including KCl in a reversed-phase column after extracting the materials from the first and last chromatograph peaks. The '714 Patent describes purified polypeptides from this process as having cytotoxic effects on human tumor cell lines as well as immunopotentiating effects, namely increasing white blood cells, T and B lymphocytes, and IgG. The compounds of the present invention are made by a process different than described in the '714 Patent, including a different starting material. The '714 Patent does not suggest dermal application of the specified polypeptides, nor use as topical agent that reduces the appearance of chronological or environmentally caused aging.

U.S. Pat. Nos. 6,087,335 and 5,824,648 are related to the '714 Patent and claim polypeptides derived from the COV-1 strain of C. versicolor having a specific partial amino acid sequence.

U.S. Pat. No. 4,202,969 describes low molecular weight (less than 5,000 kDa) nitrogen-containing polysaccharide compounds having anti-tumor activity extracted from *C. versicolor* by using a dilute alkaline solvent.

U.S. Pat. No. 4,851,395 describes a nitrogen-containing polysaccharide substantially free of units having a molecular weight below about 5,000 kDa produced by extracting *C. versicolor* with an aqueous alkaline solution (0.01 to 2.0N) at a temperature of from 50° C. to 100° C., neutralizing the resultant extract, followed by ultrafiltration or reverse osmosis to remove substantially all polymer units having a molecular weight below about 5,000 kDa.

U.S. Pat. Nos. 4,877,777, 4,900,722, and 4,975,421 assigned to BioGlucans, LP describe processes for preparing phosphorylated glucans from approximately two dozen source materials, including *C. versicolor*, in which the poly-[β-(1-3) glucopryanose]chains are phosphorylated in varying degrees by treating neutral glucans with phosphoric acid.

US Patent Application 2004/0137012 describes a pharmaceutically active agent having a molecular weight of from about 5,000 to about 20,000 useful in the treatment of diabetes where the agent is the product of hydrolysis of β(1→3) glucan derived from vegetable material, including *Coriolus*.

U.S. Pat. No. 4,614,733 discloses polysaccharides derived from *C. versicolor* having specific characteristics, including, molecular weight (from 5,000 to 300,000), infrared and nuclear magnetic resonance absorption spectra and solubility profile (soluble in water but insoluble in pyridine, chloroform, and hexane). The polysaccharides taught in the '733 Patent are made by a process comprising the steps of (i) extracting mycelia and fruit bodies of a basidiomycetous fungus, including *C. versicolor*, with an aqueous solvent, (ii) removing substances with a molecular weight of less than 5,000 by ultrafiltration and/or reverse osmosis; (iii) saturating the extract solution with ammonium sulfate; (iv) collecting the resultant precipitate, dissolving the precipitate in water, and desalting same; (v) passing the desalted solution through a column packed with an ion exchanger; (vi) concentrating and drying the solution to obtain the claimed polysaccharide.

German Patent DE 2,731,570 and related U.S. Pat. No. 4,140,578 describe nitrogen-containing polysaccharides having anti-cancer properties produced by a multi-step process involving cultivating a fungus from the genus *Coriolus* in an aqueous culture medium by submerged cultivation, drying the culture media together with the mycelia, producing an extract from the dried substance with water or an aqueous alkaline solution followed by ultrafiltration or reverse osmosis to remove substances having a molecular weight of less than 5,000.

Japanese Patent JP 52,083,996 and related U.S. Pat. Nos. 4,289,688 and 4,271,151 describe oral and intraperitoneal administration of protein-bound polysaccharides having an antitumor effect. The protein-bound polysaccharides are obtained by a process comprising the steps of concentrating an extract obtained from the mycelia and/or fruit bodies of a species of fungi belonging to the genus *Coriolus* in an aqueous solution, performing consecutive ammonium sulfate precipitations, followed by dialysis to remove salts, and finally spray-drying the desalted solution to obtain the claimed protein-bound polysaccharides.

Japanese Patent JP 09,309,842 describes an antitumor glycoprotein containing β-1,3-glucan in an amount of less than 0.001 mg/g with a molecular weight of 5,000-1,000,000 kDa from an extract of hyphae and fruiting body of *Basidiomycota* belonging to the genus *Coriolus*. The extract is obtaining by oxidation with periodic acid or its salt, followed by addition of a reducing agent, removal of low molecular compounds, and addition of β-1,3-glucanase.

Japanese Patent JP 49,048,896 describes soluble phosphorylated glucans from *C. versicolor* having a phosphorylated poly-[β-(1-3)glucopyranose] chain and its use in dermal wound healing, specifically as an agent impregnated into bandage, suture or dressing.

U.S. Pat. No. 7,048,932 describes compositions and methods for stimulating the immune system comprising administering a purified extract of *C. versicolor* having a molecular weight of 0.3 kDa to 5 kDa as determined by size exclusion chromatography and comprising at least one peptide-linked glucan in which the glucose molecules of the glucan are linked by a (1→3) linkage,. The purified extract taught in the '932 Patent is prepared by the steps of (i) treating *C. versicolor* with alkali; (ii) separating a supernatant; (iii) subjecting the supernatant to (a) cationic exchange followed by (b) anionic exchange; and (iv) collecting a fraction comprising the peptide-linked glucan.

A series of related patents assigned to Active Organics, LP—U.S. Pat. Nos. 5,976,556; 6,569,437; and 6,656,701—describe the uses of one or more acid protease enzymes in combination with an acidic buffering system that enhances epidermal exfoliation and/or epidermal cell renewal, thereby improving the texture or appearance of the skin.

Extracts of *Rhizomucor miehei* are commercially-available from a number of sources, including Novozymes, Inc. (Franklinton, N.C.), Valley Research (South Bend, Ind.) and Active Organics LP (Lewisville, Tex.), exhibit enzymatic activity, principally from acid proteases.

US Patent Application Publication No. 2007/0160563 discloses topical compositions comprising extracts of *R. miehei* that are substantially devoid of acid-protease activity and their use in treating dermatologic conditions, including reducing the appearance of signs of skin aging.

SUMMARY OF THE INVENTION

The present invention relates to an acid protease hydrolyzed polysaccharopeptide extract of *C. versicolor* that is substantially devoid of acid protease activity having anti-inflammatory properties as measured in vitro (by reduction in the level of expression of the PTGS2 gene as analyzed using DNA microarrays) and in vivo.

DETAILED DESCRIPTION OF THE INVENTION

Acid protease hydrolyzed polysaccharopeptide extract of *C. versicolor* that is substantially devoid of acid protease activity is commercially-available from the Active Organics LP under the tradename Actisoothe™ and is produced as follows: An initial fraction of *C. versicolor* is produced by mixing the macerated fruiting body of the mushroom in ethanol at a ratio of from about 1:5 to about 1:3, preferably about 1:4, for a period of from about 36 hours to about 60 hours, preferably for a period of about 48 hours. The resulting precipitate is collected and mixed with an acidic aqueous solvent, having a pH of from about 3.5 to 4.5, preferably from about 3.8 to about 4.2. The acidic aqueous solvent is made by mixing (i) citric acid (3%) and (ii) glycerin or a lower glycol, preferably propylene glycol or butylene glycol (10%) with (iii) deionized water and adjusting the pH to the desired range with a 25% solution of sodium hydroxide.

Preferably, the precipitate is present in the acidic aqueous solvent in a ratio of from about 1:50 to about 1:9, more preferably from about 1:40 to about 1:20. Deionized water is added QS. This precipitate is further extracted for period of from about 36 hours to about 60 hours, preferably for a period of about 48 hours, at a temperature of from about 30° C. to 50° C., more from about 35° C. to about 45° C.

Following this extraction period, the water-soluble polysaccharopeptide proteinaceous fraction is hydrolyzed by addition of an acid protease, preferably an acid protease of *R. miehei*, still more preferably an acid protease of *R. miehei* having from 4,000 to about 10,000 HUT units of activity per milliliter. A preferred acid protease of *R. miehei* is available under the tradename Actizyme® 3M-M from Active Organics LP. The acid protease is added as solution of from about 0.001% to 10%, preferably from about 0.01% to about 3% and more preferably from about 0.5% to about 1.5%. Hydrolysis is then conducted at a temperature of from about 35° C. to about 45° C., preferably at about 40° C., for a period of from about 36 hours to about 60 hours, preferably for a period of about 48 hours. Following hydrolysis, the acid protease is removed or inactivated by techniques well-known to those having ordinary skill in the art, including by molecular weight sieve, thermal inactivation and/or pepstatin-affinity gel chromatography.

According to one aspect of the present invention, the acid protease hydrolyzed polysaccharopeptide extract of *C. versicolor* that is substantially devoid of acid protease activity is present in a dermatologically-acceptable carrier at a concentration of from about 0.01% to about 50%, preferably at a concentration of from about 0.1% to about 10%, still more preferably at a concentration of from about 0.25% to about 5%.

One preferred aspect of the present invention is directed to topical photoprotective and anti-aging products comprising the acid protease hydrolyzed polysaccharopeptide extract of *C. versicolor* that is substantially devoid of acid protease activity at a concentration of at least about 0.1%. By photoprotective products are meant topical formulations that provide protection from ultraviolet radiation. By anti-aging products are meant topical formulations that help reduce the appearance of fine lines, wrinkles, pigment discoloration associated with chronological or environmental aging.

In Vitro Anti-Inflammatory Activity—DNA Microarray Analysis

The anti-inflammatory effect of acid protease hydrolyzed polysaccharopeptide extract of *C. versicolor* that is substantially devoid of acid protease activity is measured based on changes in the level of expression of the PTGS2 gene analyzed using DNA microarrays as described below.

Epidermal full-thickness tissue, supplied by MATEK Corporation, (Ashland, Mass.) is used for in vitro testing. Tissue samples are removed from the shipping tray, placed into a 6-well plate containing 2.5-5.0 ml of assay medium (37±2° C.), and incubated for at least 24 hours at 37±2° C. and 5±1% $CO_2$. After this initial incubation, the assay medium is replaced with 2.5-5.0 ml of fresh medium (37±2° C.). 25-50 ml of test material (test sample) and/or phosphate buffered saline (negative control) is then applied directly onto the surface of the tissue. The 6-well plates are then incubated at 37±2° C. and 5±1% $CO_2$ for 24 hours. Thereafter, the tissue samples are washed at with 100 ml of PBS and placed into a 1.5 ml centrifuge tube containing 10-12 volumes of guanidinium thiocyanate lysis solution. The tissues are minced with fine tipped scissors and homogenized until thoroughly disrupted. After homogenization, the tissues are centrifuged at 15,000 RPM for 10 minutes. The supernatant is transferred to a new tube. The pellet (tissue debris) is discarded and the tissue homogenate is then stored at −75° C. until the RNA extraction process (described below) is completed.

RNA Isolation

RNA isolation was performed using the RNAqueous Kit from Ambion Inc. (Austin, Tex.). To the cell lysates or tissue homogenates prepared above, an equal volume of 64% ethanol is added and the tubes are vortexed. Up to 700 ml of the resulting mixture is transferred to a glass fiber filter cartridge, which is loaded into a 1.5 ml collection tube and the cartridge is centrifuged for 1 minute at 14,000 RPM. The flow-through is discarded. The remaining mixture is loaded into the filter cartridge and the centrifugation process is repeated until all of the mixture is processed. The filter is then washed to remove any residual cellular debris from the RNA bound to the glass fibers by applying 700 ml of a first wash solution (1 time) and 500 ml of a second wash solution (2 times) to the filter cartridge and centrifuging at 14,000 RPM for 1 minute to pass each wash through the cartridge. The flow-through is discarded after each wash. After the final wash, one final spin is performed without wash solution to remove any residual wash solution in the filter cartridge. The RNA bound to the glass fibers within the cartridge is then eluted by applying 30 ml of Tris-EDTA buffer (Sigma) (10 mM Tris-HCl, 1 mM EDTA (Sigma), preheated to 70-80° C., hereinbelow "TE buffer") to the cartridge and centrifuging the cartridge in a new collection tube at 14,000 RPM for one minute. For samples prepared from cell lysates and small tissues, the elution process is repeated with an additional 30 ml of preheated TE buffer. For samples prepared from larger (i.e., full thickness) tissues, the elution process is repeated two additional times. After the RNA is eluted, RNA concentration is quantified using a Ribogreen assay. RNA quality is assessed via gel electrophoresis.

RNA Concentration Assay

Ribogreen reagent (NanoDrop Technologies, Wilmington, Del.) is provided as a stock solution in DMSO. Prior to use, the reagent is diluted 2000 fold in TE buffer. The RNA assay requires 200 ml of diluted Ribogreen reagent per sample to be tested and 1 ml of reagent as a standard. Once prepared, the diluted reagent is stored protected from light. A series of RNA standards are prepared by diluting purified ribosomal RNA derived from *E. coli* to the following concentrations: 2 mg/ml, 1 mg/ml, 200 ng/ml, 40 ng/ml and 0 ng/ml (blank). Prior to assaying, the RNA samples prepared above are diluted 1000 fold in TE buffer. For the RNA assay, 100 ml of the diluted samples or standards are transferred to the wells of a black 96-well plate. The samples and standards are assayed in duplicate. After the samples/standards are added to the plate 100 ml of diluted Ribogreen assay reagent is added to the wells and the plate is gently mixed and allowed to incubate for 5-10 minutes protected from the light. After this incubation, the plate is read with a fluorometer (Cole Parmer) using an excitation wavelength of 500 nm and an emission wavelength of 525 nm.

RNA Gel Electrophoresis

A 1% RNA gel is prepared by adding 0.3 g agarose to 21.6 ml diethylpyrocarbonate (DEPC) treated water. The agarose is dissolved by boiling the water in a microwave oven. After the solution is cooled to approximately 55° C., 5.4 ml of formaldehyde and 3.0 ml 10×MOPS (3-morpholinopropanesulfonic acid) (0.2 M MOPS [pH 7.0], 20 mM sodium acetate, 10 mM EDTA, made in DEPC $H_2O$) is added and filter sterilized. After mixing, the agarose gel is cast in the horizontal gel apparatus with loading slots placed on the side of the gel closest to the negative terminal. The gel is allowed to set for at least 1 hour at room temperature. While the gel is setting, 175 ml of 1×MOPS is prepared by diluting the 10× stock. After the gel is set, the comb is removed and the buffer chamber of the gel apparatus is filled with 150-175 ml 1×MOPS (enough buffer is added to cover the gel with approximately 3 mm of buffer). The cover is placed on the apparatus, the electrical leads are attached to the power source, and the empty gel is run at 40 V (4 V/cm) for 5-10 minutes. While the gel is running, the RNA samples are prepared by transferring approximately 1 mg of each sample RNA to a 600 ml PCR tube. DEPC $H_2O$ is used to bring the total volume of all the samples to a common level and then 1-3 volumes of a gel-loading buffer (i.e. 5% glycerol, 1 mM EDTA, 0.025% bromophenol blue, 0.025% xylene cyanol FF, 20% formaldehyde, 50% formamide, 10 mg/ml ethidium bromide) are added. The samples are denatured by placing them at 65-70° C. for 5-15 minutes and then placed on ice to cool. The samples are then carefully loaded into the lanes (each loading slot can hold 10-15 ml of sample, depending upon the thickness of the gel) and run on the gel at 40 V for 1-3 hours. At the end of the run, the RNA is visualized by placing the gel on a UV transilluminator (Cleaver Scientific). An RNA sample is used for subsequent processing if both the 18S and 28S ribosomal bands are clearly visible and there is little or no staining below the 18S band.

mRNA Amplification mRNA is amplified using the MessageAmp, aRNA kit from Ambion Inc. (Austin, Tex.) as follows:

First Strand cDNA Synthesis

To start the first strand synthesis, 5 mg of total RNA for each sample are added to 600 ml PCR tubes and the total volume of liquid in the tube is adjusted to 12 ml with DEPC H2O. To each tube, 1 ml of T7 Oligo(dT) primer is added and the tube is incubated at 70±2° C. for 10 minutes to denature the RNA and is then placed on ice to allow the primer to anneal to the poly A ends of the mRNA. After cooling, 2 ml of 10×first strand buffer, 1 ml of RNAse inhibitor and 4 ml of dNTP mix is added to each tube, and the tube is placed at 42° C. As soon as the tube is heated, 1 ml of reverse transcriptase is added and the tubes are returned to 42±2° C. for 2 hours. At the end of the two hours, the tubes are briefly centrifuged to collect all of the fluid at the bottom of the tube and then placed on ice.

Second Strand Synthesis and cDNA Purification

For the synthesis of the second strand of cDNA the following ingredients are added sequentially to the tubes: 63 ml DEPC $H_2O$, 10 ml 10× second strand buffer, 4 ml dNTP mix, 2 ml DNA Polymerase and 1 ml of RNAse H. The tube is mixed and then incubated at 16±2° C. for 2 hours. Towards the end of the 2 hour incubation, a sufficient quantity of DEPC $H_2O$ is warmed to 50±2° C., and a cDNA purification filter cartridge is equilibrated with 50 ml of cDNA binding buffer (one cartridge per sample) for at least 5 minutes. After the samples are finished incubating, 250 ml of cDNA binding buffer are added to each tube and thoroughly mixed. The contents of the PCR tube are then transferred to the cDNA purification filter cartridge. The cartridge is then placed in a collection tube and centrifuged at 10,000 RPM for 1 minute. The flow-through is discarded and 650 ml of cDNA wash solution is added to the cartridge. The cartridge is centrifuged again, the flow-through is discarded, and is then centrifuged one additional time to ensure that the wash buffer has been completely emptied from the filter. The cDNA is eluted by applying 10 ml of preheated DEPC H2O to the filter and centrifuging the filter in a new collection tube at 10,000 RPM for one minute. This elution is performed one additional time to give a total volume of 16-18 ml of cDNA solution.

In Vitro Transcription to Synthesize aRNA and aRNA Purification

In vitro transcription begins by adding the following to the cDNA solution: 4 ml each of T7 ATP solution, T7 CTP solution, T7 GTP solution, T7 UTP solution, 4 ml of 10×Reaction buffer, and 4 ml of T7 enzyme mix. The tube is mixed and then incubated at 37±2° C. for 6-14 hours. Towards the end of the incubation, a sufficient volume of Elution Solution is warmed to 50-60° C. and an aRNA filter cartridge is equilibrated with 100 ml of aRNA binding buffer for at least 5 minutes. At the end of the incubation period, 350 ml of aRNA binding buffer is added to the sample tubes and thoroughly mixed. An additional 250 ml of absolute ethanol is also added to each tube. The mixture is then transferred to an aRNA filter cartridge; the cartridge is then inserted into a collection tube and centrifuged at 10,000 RPM for 1 minute. The flow-through is discarded and 650 ml of aRNA wash buffer is added to the cartridge followed by centrifuging at 10,000 RPM for one minute. After discarding the flow-through, the cartridge is spun one final time to remove all traces of the wash buffer. The cartridge is then transferred to a new collection tube. 25 ml of pre-warmed Elution Solution is added to the cartridge. The cartridge is incubated for 2 minutes at room temperature and then aRNA is eluted by centrifuging for 1 minute at 10,000 RPM. This elution is performed one additional time to give a total volume of 45-50 ml of aRNA solution. The final concentration of the aRNA is determined by the Ribogreen assay described above. In addition, the quality of the aRNA is checked via gel electrophoresis as described above. An aRNA sample is used for subsequent processing if a broad band of RNA is observed.

Labeling and Purification of aRNA aRNA is labeled with fluorescent dyes using the PerkinElmer ASAP RNA Labeling Kit. Two tubes are prepared for the labeling process—for the untreated sample Cy3 labeling (green), and for the treated sample Cy5 labeling (red). To the Cy3 tube add 2 mg of aRNA prepared from the untreated/control sample and add enough DEPC H2O to bring the total volume up to 4 ml. To the Cy5 tube add 2 mg of aRNA prepared from the sample treated with the test material and add enough DEPC H2O to bring the total volume up to 4 ml. To both tubes, add 5 ml of ASAP labeling buffer and 1 ml of the specific dye for the tube (Cy3 or Cy5). Incubate the tubes for 15 minutes at 85±2° C. At the end of the 15 minutes, place the tubes on ice to cool and then add 2.5 ml of ASAP stop solution to each tube. The above proportions are sufficient for analyzing one microarray chip. If more chips are to be used then the labeling is increased proportionately.

To purify the labeled aRNA, a microcon YM-30 filter column is inserted into a collection tube and filled with 400 ml of TE buffer. The Cy3 and Cy5 probes are combined (12.5 ml of each) and then added to the microcon filter and thoroughly mixed with the TE buffer. The filter is centrifuged at 12,000 RPM for 8 minutes and the flow-through is discarded. The column is washed twice with 400 ml of TE buffer, discarding the flow though each time. After the final wash, the filter column is inverted, placed into a new collection tube and centrifuged at 12,000 RPM for 2 minutes to collect the probe (the probe is concentrated in a volume of 2-30 ml of residual TE buffer).

Microarray Hybridization and Washing

For hybridization, 45 ml of 10× control target RNA (supplied with Agilent Technologies In Situ Hybridization Kit) is mixed with 160 ml of DEPC $H_2O$ and 9 ml of 25× Agilent Fragmentation Buffer. This mixture is incubated at 60° C. for approximately 30 minutes in a hybridization oven. At the end of the incubation, 225 ml of Agilent Hybridization Buffer is added along with the fluorescent aRNA probes prepared above. The mixture is then incubated at 70° C. for 5-10 minutes in a waterbath. During this incubation period, an Agilent SUREHYB hybridization chamber is prepared by inserting a glass gasket slide into the bottom half of the chamber. At then end of the incubation, the hybridization mixture (approximately 450 ml) is applied to the glass gasket slide and an Agilent Human 1A Oligo Microarray Chip is placed face down on top of the gasket such that the hybridization solution is sandwiched between the glass gasket slide and the microarray face of the chip. The top half of the chamber is attached and the connecting thumbscrew tightened. After verifying that there is good bubble formation in the chamber, it is placed into the hybridization oven for approximately 17 hours (60° C. and rotating at 4 RPM). At then end of the hybridization period, the microarray/glass gasket is removed from the SUREHYB chamber and placed in 50 ml of a first wash solution (room temperature, 6×SSC, 0.005% Triton X-102). After the gasket has fallen away from the microarray, the array is transferred to 300 ml of fresh wash solution 1 on a magnetic stir plate. The array is washed while the solution is mixed at medium speed for 10 minutes and is then transferred to 300 ml of wash solution 2 (0.1×SSX, 0.005% Triton X-102, 4° C.) for 5 minutes. After the final wash, the array is centrifuged at 500 RPM for 5 minutes until dry.

Microarray Scanning and Analysis

The microarrays are scanned with an Axon GenePix 4100A Scanner with the scanning resolution set to 10 mm and analyzed with GenePix Pro software. During the initial scan the PMT gains for the scanner are adjusted such that the Cy5/Cy3 image count ratios are between 0.88 and 1.12.

To derive the standard curve for the Ribogreen assay, the relative fluorescent units (RFU) versus the known RNA concentrations in mg/ml for the standards is plotted and subjected to regression analysis to establish the line that best fits these data points. Mean RFU values for the test materials and untreated samples are then used to estimate the amount of RNA present in each sample. The level of gene expression is related to the fluorescence intensity of the probed gene marker on the microarray. Fluorescence measurements between the the Cy3 and Cy5 probes are normalized. The total fluorescent signal for both dyes is normalized with a correction factor such that the ratio of total intensities for both dyes equal to one.

Criteria for evaluating changes in gene expression are known to those of ordinary skill in the art and include the following: (i) the ratio of Cy3/Cy5 (untreated/treated) fluorescence intensity is greater than 1.5 or less than 0.66, corresponding to a change in gene expression of at least +/−30%; (ii) the fluorescence intensity of the gene marker is greater than the background intensity; (iii) the gene feature is clearly marked specifically by the aRNA probes and is not due to non-specific fluorescence. The first two criteria are filtered via computer analysis. The last criterion requires visual inspection of the array.

Cy3/Cy5 ratios of greater than about 1.3 are interpreted to indicate that a gene is upregulated by the treatment, whereas ratios of less than about 0.7 are interpreted to indicate a downregulated gene. Thus, a ratio of 1.3, where the treated value is 130% of the untreated value, indicates a 30% increase in gene expression. Similarly, a ratio of 0.7 means that the treated value was 70% of the untreated value, indicating a 30% decrease in gene expression.

EXAMPLE 1

Two polysaccharopeptide extracts of *C. versicolor*—the first, a hydrolyzed with acid protease of *R. miehei* and thereafter rendered substantially devoid of acid protease activity according to the methods described above, the second a non-hydrolyzed extract—were tested for the ability to reduce the level of expression of PTGS2. The acid protease hydrolyzed extract reduced the expression of mRNA coding for PTGS2 by about 67%.

In Vivo Anti-Inflammatory Efficacy

EXAMPLE 2

Reduced Erythema After UV Exposure

A gel comprising 2% by weight of extract of *C. versicolor* according to the present invention (hydrolyzed with acid protease of *R. miehei* and thereafter rendered substantially devoid of acid protease activity) and thickened with Carbopol 940, having a pH of about 6.5 was applied topically (either five minutes before or after UVR exposure) to 20 human subjects at a dose of 2-4 mg/cm². In the examples that follow, the extract of *C. versicolor* according to the present invention is referred to by its tradename, Actisoothe™. The subjects were then exposed six times over an eight-day period to 1 MED of ultraviolet radiation ("UVR") according the methodology set out in the by the FDA in the final monograph for sunscreen drug products for over-the-counter human use as published in *Federal Register* Vol. 64, No. 98, pp. 27666-27693 (May 21, 1999). One MED is the quantity of erythema-effective energy required to produce the first perceptible, redness reaction with clearly defined borders, Reduction in erythema was observed based on a* value readings from a Minolta Chroma Meter. The data presented are increases in a* values compared to pre-UVR exposure values.

| | Erythema (day 4) | Erythema (day 8) | % Reduction (day 8) |
|---|---|---|---|
| Control | 7.9 | 12.4 | NA |
| 2% Actisoothe ™ before UV | 3.4 | 6.5 | 52% |
| 2% Actisoothe ™ after UV | 5.2 | 8.2 | 34% |

EXAMPLE 3

Reduction of Stinging Response (Lactic Acid)

On twenty subjects 8% lactic acid in 80:20 ethanol:water mixture (pH 3) was applied in excess to the nasal fold area with a Q-tip type applicator. Stinging responses of the control group (no *C. versicolor* applied prior to acid application) were compared to that of the test group (2% *C. versicolor* applied). Stinging was evaluated subjectively on a 0-4 scale over a 20 minute time period (time=0, 1, 2, 5, 8, 14, 20 minutes). Scores were summed and presented as initial and delayed sting:

| Test Panel | Treatment | Initial | Delayed | Total Sting | % Reduction |
|---|---|---|---|---|---|
| Control | none | 2.3 | 4.9 | 7.2 | NA |
| Control | 2% Actisoothe | 2.2 | 4.2 | 6.4 | 11% |

EXAMPLE 4

Reduction of Erythema (Balsam of Peru)

Balsam of Peru, a know contact irritant, was applied to the skin of subjects. Erythema was measured using a Minolta Chroma Meter (a* value). After five days of treatment with the 2% (Actisoothe™), the test group (*C. versicolor* applied) showed an increased resistance to Balsam of Peru application of 25% over the control group (no *C. versicolor* applied).

| Test Panel | Treatment | Increase in Erythema (Δ*a) | % Reduction |
|---|---|---|---|
| Control | none | 44.5 | NA |
| Test | 2% Actisoothe | 32.3 | 25% |

EXAMPLE 5

Reduction of Skin Reactivity (Methyl Nicotinate)

Skin reactivity, measured as an erythemic response (measured as visually identifiable redness) was tested by topical application of methyl nicotinate (Sigma Aldrich) in increasing concentrations until a measurable erythemic response was observed. Test groups (2% *C. versicolor* applied) required a 25% increase in dose of methyl nicotinate to induce an erythemic response than did the control group (no *C. versicolor* applied).

| Test Panel | Treatment | Concentration Inducing Erythema | % Change |
|---|---|---|---|
| Control | none | 0.084 | NA |
| CIS Group | none | 0.025 | NA |
| Control | 2% Actisoothe ™ | 0.103 | +25% |
| CIS Group | 2% Actisoothe ™ | 0.065 | +160% |

EXAMPLE 6

Reduction of Cosmetic Intolerance Syndrome (CIS)

Test subjects with CIS, self identified and exhibiting at least one moderate to severe cosmetic product reaction (cosmetic acne, product related erythema, transitory itching or burning, allergic response, or contact dermatitis) within the past six months were recruited for this study. While the CIS group did not have a significantly higher rate of transepidermal water loss (TEWL) rate compared to the control they exhibited a more pronounced response when exposed to a topical irritant—specifically 8% lactic acid pH 3 applied in excess to the nasal fold area in an 80:20 ethanol:water vehicle. Stinging was evaluated subjectively on a 0-4 scale every minute for 5 minutes, thereafter every three minutes until 20 minutes (e.g., at time=8, 11, 14, 17 and 20 minutes). Scores were summed and presented as initial and delayed sting scores. After five days of treatment with a 2% Actisoothe™ gel (at a dose of 5 mg product/cm² twice a day) the CIS group showed a 31% reduction in sting response:

| Test Panel | Treatment | Initial | Delayed | Total Sting | % Reduction |
|---|---|---|---|---|---|
| Control | none | 2.3 | 4.9 | 7.2 | NA |
| CIS Group | none | 4.3 | 9.1 | 13.4 | NA |
| Control | 2% Actisoothe | 2.2 | 4.2 | 6.4 | 11% |
| CIS Group | 2% Actisoothe | 3.3 | 6.1 | 9.4 | 31% |

Anti-inflammatory compositions according to the present invention may optionally include (in addition to extract of *C. versicolor* hydrolyzed with acid protease of *R. miehei* and thereafter rendered substantially devoid of acid protease activity) one or more steroidal or non-steroidal anti-inflammatory drug (NSAID) known to those of ordinary skill in the art. Preferred examples of NSAIDS include propionic acid derivatives, acetic acid derivatives, fenamic acid derivatives, biphenylcarboxylic acid derivatives, and oxicams. The Cosmetic, Toiletries & Fragrance Association, *International Cosmetic Ingredient Dictionary and Handbook*, Vol. 11, p. 1364 (11$^{th}$ Edition, 2006) ("CTFA Dictionary") describes a wide variety of non-limiting cosmetic and pharmaceutical ingredients commonly used in the skin care industry, which are also suitable for use in combination with the extract of *C. versicolor* hydrolyzed with acid protease of *R. miehei* and thereafter rendered substantially devoid of acid protease activity as claimed in the present application.

The following formulation examples are further illustrative of the present invention. The components and specific ingredients are presented as being typical, and various modifications can be derived in view of the foregoing disclosure within the scope of the invention. All percentages, ratios and proportions herein are by weight, unless otherwise specified. All temperatures are in degrees Celsius unless otherwise specified.

FORMULATION EXAMPLE 1

Toner

| | |
|---|---|
| Deionized Water | 93.190% |
| Methyl Gluceth-20 | 1.000% |
| Potassium Sorbate | 0.100% |
| Sodium Benzoate | 0.100% |
| Phenoxyethanol | 0.600% |
| Citric acid | 0.010% |
| Extract of *C. versicolor* hydrolyzed with acid protease of *R. miehei* and thereafter rendered substantially devoid of acid protease activity | 5.000% |

Add ingredients sequentially in order listed. Mix until clear. End processing.

FORMULATION EXAMPLE 2

Face Cream

| | |
|---|---|
| Part A | |
| Deionized Water | 62.600% |
| Magnesium Aluminum Silicate | 0.400% |
| Xanthan Gum | 0.150% |
| Acrylates/C$_{10-30}$ Alkyl Acrylate Crosspolymer | 0.750% |
| Part B | |
| Butylene Glycol | 4.000% |
| Disodium EDTA | 0.050% |
| Part C | |
| Hydrogenated Lecithin | 0.500% |
| Caprylic/Capric Triglyceride | 8.000% |
| Simmondsia Chinensis (Jojoba) Seed Oil | 5.000% |
| Octyl Palmitate | 4.000% |
| Cetearyl Alcohol | 2.000% |
| PEG-8 Stearate | 1.000% |
| PEG-100 Stearate | 0.800% |

-continued

| Part D | |
|---|---|
| Triethanolamine 99% | 0.100% |
| Part E | |
| *Aloe Barbadensis* Leaf Juice (Activera ® 10x, Active Organics) | 5.000% |
| Phenoxyethanol | 0.500% |
| Potassium Sorbate | 0.100% |
| Methylisothiazolinone | 0.050% |
| Extract of *C. versicolor* hydrolyzed with acid protease of *R. miehei* and thereafter rendered substantially devoid of acid protease activity | 5.000% |

Sprinkle Magnesium Aluminum Silicate, Xanthan Gum, Acrylates/$C_{10-30}$ Alkyl Acrylate Crosspolymer into vortex of water. Mix and heat to 80° C. Add Part B to Part A, mix and hold the temperature at 80° C. In a separate vessel, mix Part C and heat to 75° C., mix until clear. Add Part C to Parts A and B, mix for 10 minutes. Add Part D to Parts ABC. Mix for 15 minutes. Switch to sweep mixing. Cool batch to 45° C. In a separate container, add ingredients in Part E. Mix until uniform. At 45° C., add Part E, to Parts ABCD. Mix and cool to 25° C. End processing.

FORMULATION EXAMPLE 3

Eye Cream

| Part A | |
|---|---|
| Deionized Water | 57.650% |
| Acrylates/C10-30 Alkyl Acrylate Crosspolymer | 0.300% |
| Panthenol | 0.100% |
| Potassium Sorbate | 0.100% |
| Disodium EDTA | 0.100% |
| Allantoin | 0.100% |
| Part B | |
| Caprylic/Capric Triglyceride | 2.000% |
| Dimethicone | 3.000% |
| *Butyrospermum Parkii* (Shea Butter) | 2.000% |
| *Carthamus Tinctorius* (Safflower) Seed Oil | 2.000% |
| Cetearyl Alcohol | 1.500% |
| Dimethiconol | 1.300% |
| Steareth-2 | 1.000% |
| Steareth-21 | 0.500% |
| Cyclomethicone | 5.000% |
| Part C | |
| Triethanolamine | 0.250% |
| Part D | |
| Carbomer 940 2% Solution | 10.000% |
| Part E | |
| *Mucor Miehei* Extract, Butylene Glycol, and N-Acetylglucosamine | 5.000% |
| Part F | |
| Sodium Hyaluronate (Actimoist ® Bio 2, Active Organics) | 2.000% |
| Phenonip | 1.000% |
| *Aloe Barbadensis* Leaf Juice (Activera ® 10X, Active Organics) | 5.000% |
| Tocopherol | 0.100% |

Sprinkle Acrylates/$C_{10-30}$ Alkyl Acrylate Crosspolymer into vortex of water. Mix and heat to 75° C. Mix and heat Part B to 70° C. Add Part B to Part A, mix for 10 minutes. Add Part C. Mix for 10 minutes. Add Part D. Mix and cool to 45° C. At 45° C., add Parts E and F. Mix and cool to 25° C. End processing.

FORMULATION EXAMPLE 4

Lipstick

| Part A | |
|---|---|
| *Ricinus Communis* (Castor) Seed Oil | 24.37% |
| Octyl Palmitate | 33.33% |
| Petrolatum | 10.84% |
| Beeswax | 3.33% |
| Paraffin Wax | 3.33% |
| *Euphorbia Cerifera* (Candelilla) Wax | 5.20% |
| Ozokerite | 3.00% |
| *Copernicia Cerifera* (Carnauba) Wax | 2.50% |
| *Simmondsia Chinensis* (Jojoba) Seed Oil | 8.00% |
| Propylparaben | 0.10% |
| Part B | |
| Polyglyceryl-4 Isostearate | 1.00% |
| *Mucor Miehei* Extract, Butylene Glycol, and N-Acetylglucosamine | 5.00% |

Mix and heat Part A to 80° C. Pre-mix Part B; add to Part A. Mix and pour into container.

FORMULATION EXAMPLE 5

Face Mask

| Part A | |
|---|---|
| Deionized Water | 59.960% |
| *Aloe Barbadensis* Leaf Juice (Activera ™ 10X, Active Organics) | 5.000% |
| Glycerin | 4.000% |
| Caffeine | 0.100% |
| *Acacia* Gum | 0.300% |
| Chromium Oxide Green | 0.500% |
| Titanium Dioxide | 3.000% |
| Methylparaben | 0.200% |
| Part B | |
| Glyceryl Stearate | 6.000% |
| *Simmondsia Chinensis* (Jojoba) Seed Oil | 1.500% |
| Tocopheryl Acetate | 0.100% |
| Propylparaben | 0.100% |
| Part C | |
| Bentonite | 11.000% |
| Part D | |
| Phenoxyethanol | 0.500% |
| Citric Acid 50% | 2.100% |
| Extract of *C. versicolor* hydrolyzed with acid protease of *R. miehei* and thereafter rendered substantially devoid of acid protease activity | 5.000% |
| Part E | |
| Essential Oil (Spearmint) | 0.070% |
| Essential Oil (Peppermint) | 0.070% |

Mix and heat Part A to 75° C. Mix and heat Part B to 75° C. Homogenize Part A, then add Part B continuing, mixing in the homogenizer for 5 minutes. Start to cool. At 60° C., add Part C; mix well. Continue cooling. At 45° C., add Parts D and E. Mix and cool to 25° C. End processing.

FORMULATION EXAMPLE 6

Moisturizing Shampoo

| Part A | |
|---|---|
| Deionized Water | 46.680% |
| Aloe Barbadensis Leaf Juice (Activera ® 10X, Active Organics) | 10.000% |
| Part B | |
| Sodium C14-16 Olefin Sulfonate | 18.000% |
| Cocamidopropyl Betaine | 18.000% |
| Glucamate DOE-120 | 1.000% |
| Part C | |
| Phenoxyethanol | 0.300% |
| Kathon CG | 0.020% |
| Sodium Chloride 25% Solution | qs |
| Butylene Glycol and Spiraea Ulmaria Extract (Actiphyte ® Queen of Meadow Concentrate, Active Organics) | 1.000% |
| Part D | |
| Extract of C. versicolor hydrolyzed with acid protease of R. miehei and thereafter rendered substantially devoid of acid protease activity | 5.000% |

Mix and heat Part A to 50° C. Add Part B to Part A; mix until clear. Add Parts C and D to Parts A and B. Mix and cool to 25° C. End processing.

FORMULATION EXAMPLE 7

Moisturizing Conditioner

| Part A | |
|---|---|
| Deionized Water | 64.670% |
| Aloe Barbadensis Leaf Juice (Activera ® 10X, Active Organics) | 5.000% |
| Panthenol | 0.200% |
| Part B | |
| Jojoba Oil | 2.000% |
| Behentrimonium Methosulfate, Cetearyl Alcohol | 4.000% |
| Stearamidopropyl Dimethylamine | 2.000% |
| Cetearyl Alcohol | 4.500% |
| PEG-100 Stearate | 0.880% |
| Glyceryl Stearate | 1.200% |
| Part C | |
| Water, Phenyl Trimethicone, Cyclomethicone, Polysilicone-11, Lecithin (Actiprime ™ 100, Active Organics) | 10.000% |
| Part D | |
| Extract of C. versicolor hydrolyzed with acid protease of R. miehei and thereafter rendered substantially devoid of acid protease activity | 5.000% |
| Phenoxyethanol | 0.500% |
| Methylisothiazolinone | 0.050% |

Mix and heat Part A to 75° C. Mix and heat Part B to 75° C. Add Part B to Part A. After mixing, add Part C and mix. Cool until 45° C., then add Part D. Mix and cool to 25° C. End processing.

FORMULATION EXAMPLE 8

Face Serum

| Part A | |
|---|---|
| Deionized Water | 80.850% |
| Keltrol RD | 0.250% |
| Butylene Glycol | 0.400% |
| Part B | |
| Water | 0.600% |
| Potassium Sorbate | 0.100% |
| Part C | |
| Water, Algae Extract, and Aloe Barbadensis Leaf Juice (Actisea ® 100, Active Organics) | 5.0% |
| Part D | |
| Aloe Barbadensis Leaf Juice (Activera ® 10x, Active Organics) | 5.000% |
| Phenoxyethanol | 0.600% |
| Neolone 950 | 0.050% |
| Extract of C. versicolor hydrolyzed with acid protease of R. miehei and thereafter rendered substantially devoid of acid protease activity | 5.000% |
| Part E | |
| Water | 2.000% |
| Allantoin | 0.1% |
| Disodium EDTA | 0.05% |

Mix Part A. Add pre-dissolved Part B; mix until uniform. Add Part C; mix until uniform. Add Part D; mix well. Add pre-dissolved Part E, mix until uniform. End processing.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A topical anti-inflammatory mushroom hydrolysate substantially devoid of acid protease activity produced by the steps of (a) extracting Coriolus versicolor in an acidic aqueous solvent having a pH of from about 3.5 to about 4.5 to form a water-soluble polysaccharopeptide extract, (b) hydrolyzing the water-soluble polysaccharopeptide extract with an acid protease enzyme of Rhizomucor miehei and, (c) inactivating or removing the acid protease via molecular weight sieve, thermal inactivation and/or pepstatin-affinity gel chromatography.

2. The topical anti-inflammatory mushroom hydrolysate substantially devoid of acid protease activity according to claim 1 wherein the acid protease enzyme of Rhizomucor miehei used to hydrolyze the water-soluble polysaccharopeptide extract of *Coriolus versicolor* has from about 4,000 to about 10,000 HUT units of activity per milliliter.

3. A dermatocosmetic composition comprising from about 0.01% to about 10% by weight of the topical anti-inflammatory mushroom hydrolysate according to claim 1.

4. A dermatocosmetic composition comprising the topical anti-inflammatory mushroom hydrolysate according to claim 1, further comprising at least one additional topical anti-inflammatory agent.

5. The dermatocosmetic composition of claim 4 wherein the at least one additional topical anti-inflammatory agent is a non-steroidal anti-inflammatory drug.

6. The dermatocosmetic composition of claim 4 wherein the at least one additional topical anti-inflammatory agent is hydrocortisone.

7. A method for inhibiting the production of COX-2 enzymes comprising applying to the skin of a mammal a therapeutically-effective amount of the topical anti-inflammatory mushroom hydrolysate according to claim 1.

8. The method of claim 7, wherein the topical anti-inflammatory mushroom hydrolysate of claim 1 is applied in a concentration sufficient to reduce the expression of mRNA coding for PTGS2 by at least about 50%.

9. The method of claim 7, wherein the topical anti-inflammatory mushroom hydrolysate of claim 1 is applied in a concentration sufficient to reduce the expression of mRNA coding for PTGS2 by at least about 67%.

* * * * *